United States Patent [19]

Kaster

[11] 4,366,819
[45] Jan. 4, 1983

[54] ANASTOMOTIC FITTING

[76] Inventor: Robert L. Kaster, 2730 Vagabond La., Plymouth, Minn. 55447

[21] Appl. No.: 207,676

[22] Filed: Nov. 17, 1980

[51] Int. Cl.³ .............................................. A61B 17/04
[52] U.S. Cl. ................................................ 128/334 C
[58] Field of Search ............... 128/334 R, 334 C, 283, 128/348

[56] References Cited

U.S. PATENT DOCUMENTS

| 2,453,056 | 11/1948 | Zack | 128/334 C |
| 3,435,823 | 4/1969 | Edwards | 128/334 C |
| 3,540,451 | 11/1970 | Zeman | 128/334 R |
| 3,774,615 | 11/1973 | Lim et al. | 128/334 C |

Primary Examiner—Michael H. Thaler
Attorney, Agent, or Firm—Hugh D. Jaeger

[57] ABSTRACT

Anastomotic fitting for coronary artery bypass graft surgery having an assembly of four components including a cylindrical tube having at least one ringflange locking indentation in an inflow end and a plurality of locking ring grooves in an outflow end, a ringflange having a central aperture and pluralities of long and short spikes, the long spikes engaging in the locking indentation, with a graft engaged therebetween, a fixation ring having a central aperture and a plurality of spikes positioned about the aperture, and a locking ring having an aperture with a plurality of locking ring ridges for engagement with the locking ring grooves. At surgical implantation an aortic wall having a hole therein engages between the ringflange and the fixation ring and is held in position by the spikes of the fixation ring, and the four components engage together forming an integral anastomotic fitting. A first alternative embodiment includes a three-component anastomotic fitting having a combination fixation ring-locking ring. A second alternative embodiment includes a four-component anastomotic fitting having a slightly flared end at an inflow end yielding a larger exposure of graft material at the anastomotic ostium.

15 Claims, 10 Drawing Figures

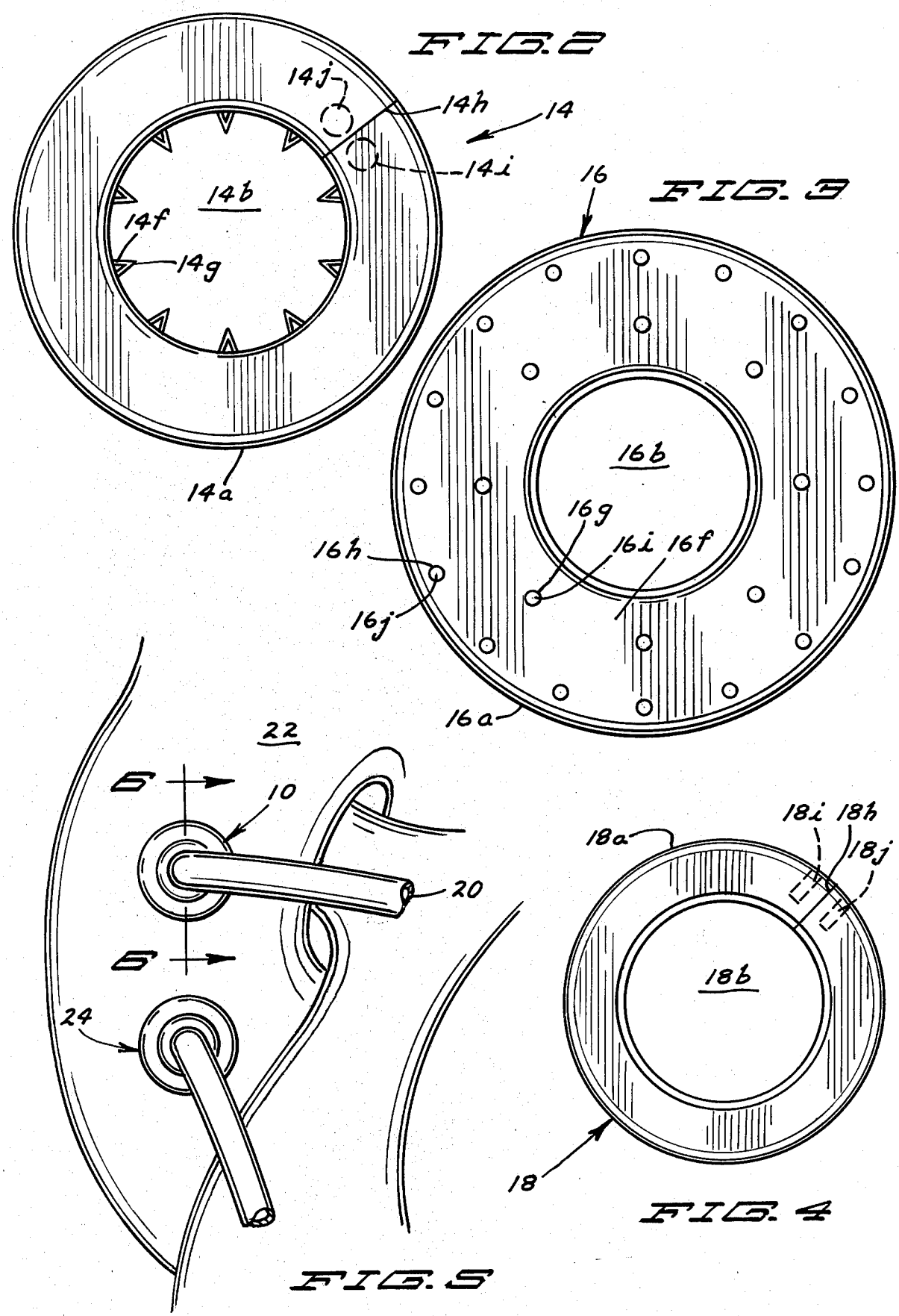

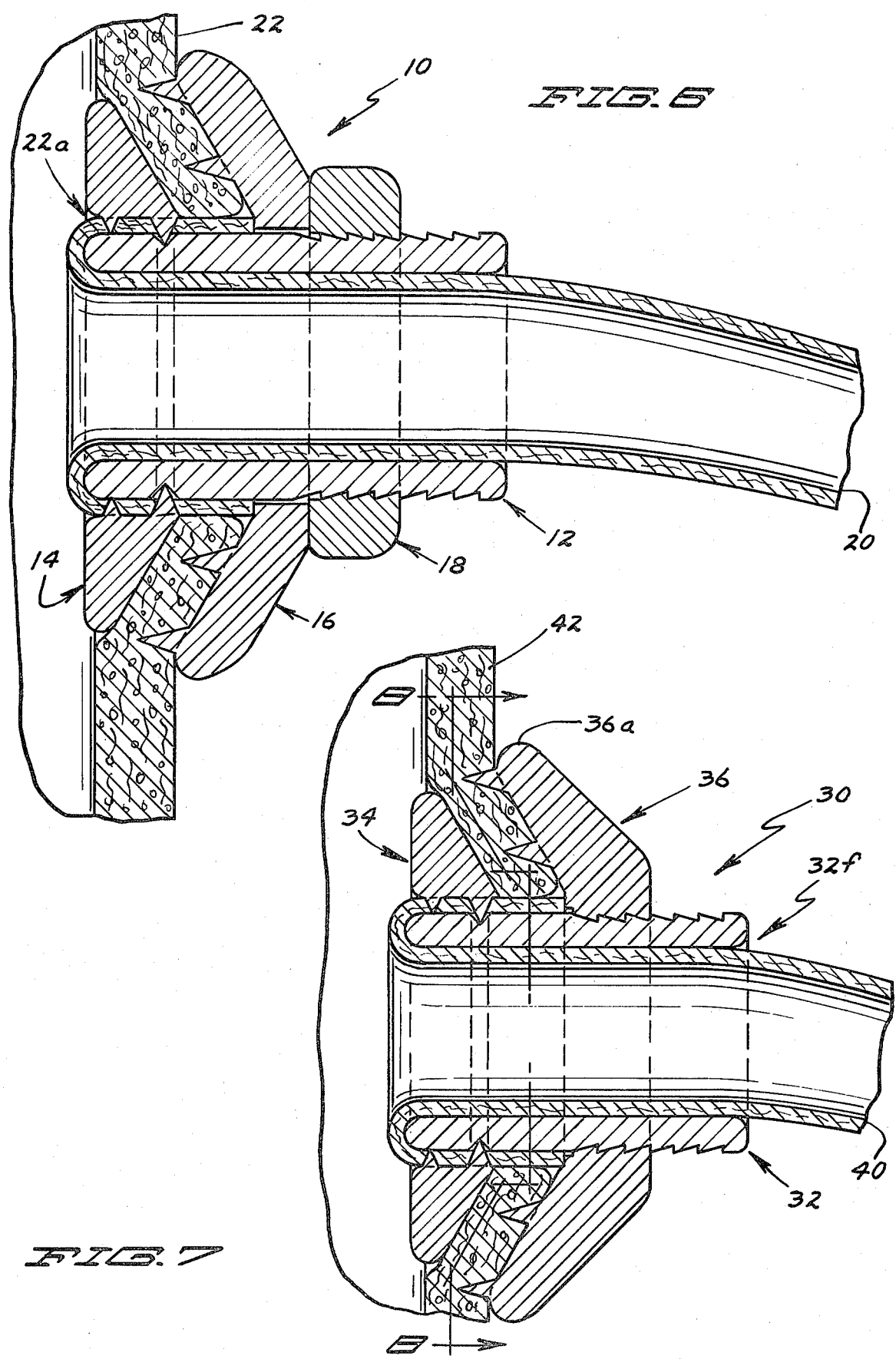

ANASTOMOTIC FITTING

BACKGROUND OF THE INVENTION

1. Field of the Invention

The present invention pertains to a surgical prosthesis, and, more particularly, pertains to an anastomotic fitting for connecting a vascular graft to the wall of the ascending aorta.

2. Description of the Prior Art

Diseases affecting the cardiovascular system are either congenital or acquired. An acquired cardiovascular disease can result from living habits, infections or injuries during embryonic life, or at any time following birth. Some diseases primarily affect the blood vessels; others only the heart itself.

Atherosclerosis is the major disease that affects the blood vessels. This disease may have its beginnings early in life and is first noted as a thickening of the arterial walls. This thickening is an accumulation of fat, fibrin, cellular debris and calcium. The resultant narrowing of the internal lumen of the vessel is called stenosis. Vessel stenosis impedes and reduces blood flow. Hypertension and dysfunction of the organ or area of the body that suffered the impaired blood flow can result.

As the buildup on the inner wall of a vessel thickens, the vessel wall loses the ability to expand and contract. Also, the vessel loses its viability and becomes weakened and susceptible to bulging, also known as aneurysm. In the presence of hypertension or elevated blood pressure, aneurysms will frequently dissect and ultimately rupture.

Small vessels, such as the arteries that supply blood to the heart, legs, intestines and other areas of the body, are particularly susceptible to atherosclerotic narrowing. The loss of blood supply to the leg or segment of the intestine may result in gangrene. Atherosclerotic narrowing of the coronary arteries impedes, limits and in some instances prevents blood flow to regional areas of the heart. Depending upon its severity and location within the coronary circulation, pain, cardiac dysfunction or death may result.

Vascular complications produced by atherosclerosis, such as, stenosis, aneurysm, rupture and occlusion are, in the majority of cases, managed either medically or surgically. Control and elimination of hypertension is the more effective form of medical management. In cases in which atherosclerotic disease is advanced and the attendant complications jeopardize the health of the patient, surgical intervention is usually instituted.

Aneurysms and stenosis of major arteries are best corrected by a plastic reconstruction that does not require any synthetic graft or patch materials. However, if the disease is extensive and the vessel is no longer reliable, it is usually replaced by a graft. In such cases, the involved vessel section is transected and removed and a synthetic patch, conduit or graft is sewn into place.

Medium sized arteries are operated on much the same as for large diameter vessels. But in some types of surgery where the replacement graft is of small diameter, handling and surgical placement of the graft is difficult. The internal diameter may be compromised due either to surgical technique or biological response. In some cases, the graft may become entirely occluded shortly after surgery.

Patients with coronary artery disease in which blood flow to part of the heart muscle has been compromised receive significant benefit from coronary artery bypass surgery. This type of surgery requires the use of grafts of small diameter. These grafts, the majority of which are biologic, have certain inherent problems. Synthetic grafts are only used on infrequent occasions because they are more problematical than biologic grafts. It is the purpose of this invention to obviate and eliminate certain of the more significant problems associated with the surgical procedure of coronary artery bypass and the implanted grafts following surgery.

In a patient who undergoes coronary artery bypass surgery, a non-critical artery or vein of small diameter is harvested from elsewhere in the body and sewn into place in a manner that reestablishes flow to the area of the heart that earlier lost its blood supply because of atherosclerotic blockage and is referred to as an autograft. When no suitable artery or vein can be harvested, an allograft or xenograft vessel may be employed. However, experience with these latter two graft types is limited because of unsatisfactory results. A synthetic graft is an alternative to an allograft or a xenograft. But, like the allograft and xenograft, the synthetic counterpart does not produce acceptable results.

Although the heart benefits immediately from the reestablished blood supply of the bypass, there is no assurance the graft will function trouble free indefinitely. The autograft, because it is harvested from the patient, who in all probability is being operated on for atherosclerotic artery disease, is highly susceptible to atherosclerosis following surgery. Most harvested veins used in coronary artery bypass surgery exhibit some degree of atherosclerosis.

The long vein in the leg called the saphenous vein is the most commonly harvested vein for use as a vein bypass graft, in coronary artery surgery. Most saphenous vein bypass grafts, in time, exhibit a narrowing of the lumen unlike that of atherosclerosis. It is believed this is a pathologic response of the vein because it is of different cellular construction and composition than an artery—a condition for which it is not best suited. Harvesting a saphenous vein autograft is a tedious surgical task and not always rewarded with the best quality graft. Also, removal of the saphenous vein disrupts the natural venous blood return from the leg and is not therapeutically recommended except for medical reasons such as in a patient with advanced venous diseases such as varicose veins. Finally, harvesting an autograft in the operating room requires additional surgical time and expense.

These noted limitations of the saphenous vein autograft have generated interest in a synthetic graft for coronary artery bypass. Clinical experience with small diameter synthetic grafts for coronary artery bypass dates back to the mid 1970's. Teflon and Dacron fibers are the most commonly employed materials for synthetic grafts. However, despite the different methods and techniques of graft construction such as woven or knit, velour, texturized or non-texturized, tight or loose, fine or coarse, expanded or non-expanded, variations in fiber diameter and wall thickness, etc., no graft of small lumen diameter has shown a resistance to blockage by thrombus. However, synthetic grafts of large diameter consistently remain patent and trouble-free for extended periods of many years. This finding is consistently repeated where a small-diameter synthetic graft is used to bypass a blocked coronary artery. Therefore, despite their inherent limitations, autografts employing the saphenous vein remain the graft of choice for coronary artery bypass surgery.

The coronary artery circulation begins with the right and left coronary arteries. These two arteries in turn give rise to an extensive coronary circulation. Generally, atherosclerosis affects the larger coronary arteries. Therefore, a patient being operated upon for coronary artery disease will receive two or more vein grafts of various length and diameter depending upon the location of the blockage and the usable harvested saphenous vein.

Even though coronary artery bypass surgery is widely practiced and has become a routine procedure in hospitals throughout the world, it is not without certain operative limitations that would best be avoided. Sewing the graft to the host vessel, known as an anastomosis, requires delicate surgical techniques to accomplish the best possible result. There are several complications to be avoided when anastomosing a vessel and graft together. It is important that the junction between the host tissue and graft be a uniform transition without narrowing and regional irregularities such as protuberances that bulge into the lumen or sinuses that extend outward of the lumen. A narrowing at the site of anastomosis reduces blood flow. Protuberances into the lumen obstruct blood flow and may produce turbulence. Lastly, blood that stagnates in a sinus or cavity tends to clot and obstruct the vessel lumen and subsequently the blood flow. All these characteristics diminish the effectiveness and patency of the graft.

Summarizing, the limitations associated with the autograft is applied in coronary artery bypass surgery are: tedious surgical task to harvest, physically imperfect and irregular lumen, tedious surgical task to anastomose to host vessel, physically imperfect anastomosis of irregular and unsmooth transition between graft and vessel, functioning narrowing of vein graft lumen during early postoperative period, and occlusion of the autograft due to thrombosis and/or continuance of the pre-existing atherosclerotic process.

The anastomotic fitting of the present invention provides a device simplifying the surgical task of implanting coronary artery bypass grafts and of connecting two vessels to each other. The anastomotic fitting provides a connection between the ascending aorta and a graft with smooth wall contours that are not obstructive to the natural flow of the blood.

SUMMARY OF THE INVENTION

The general purpose of the present invention is an anastomotic fitting for connecting a vascular graft to the ascending aorta, and providing for a uniform ostium having a smooth surface throughout from the aortic wall to the graft. The anastomotic fitting accepts either a saphenous vein graft or a synthetic vascular graft, and is utilized in connecting a vascular graft of a first diameter to a blood vessel of second diameter. While the blood vessel of a first diameter is usually of a lesser diameter than a blood vessel of a second diameter, the vessels can be of equal diameters or, in the alternative, the first diameter can be greater than a second lesser diameter. The anastomotic fitting includes a cylindrical tube through which the vascular graft engages and overlaps at an inflow end where a ringflange spatially engages the overlapped end with the inflow end of the tube. The anastomotic fitting engages in position in a hole in the aortic wall by the ringflange engaging against the inside aortic wall about the hole and by the fixation ring including a plurality of outward extending spikes engaging against the outside aortic wall about the hole.

According to one embodiment of the present invention, there is provided an anastomotic fitting for connection between an aortic wall and a vascular graft including a cylindrical tube having a lumen extending therethrough, a ringflange circumferential indentation adjacent an inflow end of the tube and a plurality of locking ring grooves adjacent an outflow end of the tube; a ringflange having a circular member with a concentric central aperture larger than the outer diameter of the tube therethrough, and a triangular right-angle cross-section where the base is substantially parallel to the aortic wall, the hypotenuse engages against the inside aortic wall surface and the base includes a plurality of inwardly extending short and long spikes, the short spikes engaging the vascular graft at a plurality of points and the long spikes engaging through the vascular graft into the ringflange indentation; a fixation ring having a circular member with a central aperture therethrough and a truncated cone cross-section and pluralities of rows of outwardly extending spikes, the spikes partially engaging into the outside aortic wall, and the central aperture larger than the outer diameter of the tube; and, a locking ring having a circular member with a central aperture slightly larger than the outer diameter of the tube, and a plurality of inwardly extending locking ring ridges whereby a hole is surgically positioned in the aortic wall, the vascular graft is positioned through the tube and overlapped about the inflow end, the ringflange is engaged about the overlapped end and into the ringflange locking indentation, the partially assembled fitting is inserted and engaged within the hole and against the inside of the aortic wall, the fixation ring is engaged about the tube and against the outside of the aortic wall, and the locking ring is engaged against the locking grooves of the tube thereby providing for communication of the vascular graft with the aorta, and the other end of the vascular graft is surgically sutured to a remote artery or connects to another anastomotic fitting of different configurations positioned in a remote artery.

According to another alternative embodiment of the present invention, there is provided an anastomotic fitting including a combined fixation-locking ring whereby the fixation ring and locking ring of the previous embodiment described above are incorporated into a single integral unit thereby providing a three-component anastomotic fitting.

According to an additional embodiment of the present invention, there is provided an anastomotic fitting including a tube with a flared end, a ringflange which engages a vascular graft between short spikes of the ringflange and the flared end and long spikes of the ring flange and a circumferential ringflange indentation in the tube, a fixation ring, and a locking ring thereby providing a four-component anastomotic fitting structurally similar to that of the anastomotic fitting previously described.

Vascular graft is encompassing in definition including biologic grafts being either human or animal and synthetic grafts, and is not to be construed as limited to a saphenous vein graft which is discussed by way of example and for purposes of illustration only. Synthetic grafts can include woven materials of synthetic plastics, processed biologic materials, or composite metals.

One significant aspect and feature of the present invention is a precision ostium providing for facilitated surgical implantation, and safety and efficacy in vivo. The precision nature of the ringflange with engagement of the inflow orifice of the tube provides a high-quality and consistent ostium. The ringflange lies flat against the inside of the aortic wall and the peripheral edges are rounded, thereby reducing turbulence and aortic flow velocity. The resultant ostium exhibits surface contours of least variation from the aortic wall to the vascular graft. On account of the minimal surface projection of the ringflange, there results a full orifice ostium and a nonrestrictive direct flow path from the aorta. Coronary hemodynamics are superior to that of conventional hand-stitched anastomosis. The anastomotic fitting includes geometrical components that engage in a predetermined relationship forming an integral unit, and that are subject to no movement following surgical implant. The 90° angle of exit from the aorta ensures maximum protection against thrombosis. In the event the aorta is thickened and/or calcified from extensive atherosclerotic disease, the anastomotic fitting provides for safe and effective attachment of a vascular graft. Another significant aspect and feature of the present invention is an anastomotic fitting that provides for least surgical implant time and motion, that minimizes the influence of tissue and operative variables. The steps required for surgically implanting the anastomotic fitting are simple, least time consuming, and more readily mastered than that of creating an anastomosis with a saphenous vein by the tedious hand-stitching methods. The resultant ostium is always circular and includes smooth inflow contours.

A further significant aspect and feature of the present invention is an anastomotic fitting which can be installed in less time, with greatest efficiency, and the utilization of fewest consumable supplies, equipment and expense. The assembled component anastomotic fitting assures a tight, patent anastomotic fitting that enables both the aortic wall tissue around the hole and the saphenous vein if utilized to receive nutrients from the blood and remain viable. If for any reason the anastomotic fitting requires reinstallation, relocation, or removal, the fitting can readily and easily be removed in least time without damage to surrounding tissue of the aortic wall about the hole. Most importantly, the anastomotic fitting is adjustable to the friability of the aortic wall.

Having thus described the invention, it is a principal object hereof to provide an anastomotic fitting for connecting or reconnecting a vascular graft of first diameter to a blood vessel of second diameter, particularly in coronary artery bypass surgery.

An object of the present invention is an entire blood flow path which is constructed of natural material. The entire blood flow path from the ostium that confronts the aortic lumen and onward over the entire length of the bypass graft is the natural blood compatible surface of the lumen of the saphenous vein. Inverting the saphenous vein graft over the end of the tube produces a superior anastomotic ostium. The ringflange is the only minimal foreign surface exposed to the blood and presents no adverse effect or influence on the long-term patency of the ostium or graft, especially when constructed of the highly blood-compatible material Pyrolite.

Another object of the present invention is an anastomotic fitting providing an unimpeded blood flow path of smooth transitional flow contours that reduces the effects of turbulence. The ringflange that engages against the internal aortic wall provides minimal blood flow obstruction, turbulence and stagnation. The anastomotic fitting also provides an external configuration that conforms with adjacent vessels and the limited available space in the chest cavity in the region of the heart.

Another object of the present invention is an anastomotic fitting including a ringflange that accepts vascular grafts including saphenous vein grafts of widely varying thickness. The ringflange effectively engages saphenous vein grafts of a wide range of thicknesses and retains the grafts in frictionally engaged surface contact with the inflow end of the tube providing for unrestricted, natural circulation throughout the engaged tissues. Also the ringflange and fixation collar accept varying thicknesses of the aortic wall. The full orifice ostium is not narrowed and is not obstructive to blood flow from the aorta into the graft.

An additional object of the present invention is a patent lumen providing support for the full orifice anastomotic ostium where the tube also provides shielding protection for the first several millimeters of the graft. This prevents external forces such as intrathoracic pressures, blood flow pulsations and twisting of the graft from impinging on the anastomosis or first few millimeters of the graft. This reduces the potential narrowing of the ostium and occlusion of the lumen.

A further object of the present invention is an anastomotic fitting that engages the hole surrounding the aortic wall and that of the saphenous vein or other biologic tissue vascular graft resulting in uninterrupted vascular circulation and blood supply to the tissues. The tissues therefore remain viable and the efficacy of the anastomosis is preserved.

BRIEF DESCRIPTION OF THE DRAWINGS

Other objects and many of the attendant advantages of this invention will be readily appreciated as the same becomes better understood, by reference to the following detailed description when considered in connection with the accompanying drawings, in which like reference numerals designate like parts throughout the figures thereof and wherein:

FIG. 2 illustrates a sectional view taken along line 2—2 of FIG. 1;

FIG. 3 illustrates a sectional view taken along line 3—3 of FIG. 1;

FIG. 4 illustrates a sectional view taken along line 4—4 of FIG. 1;

FIG. 5 illustrates two anastomotic fittings positioned in the aortic wall;

FIG. 6 illustrates a sectional view taken along line 6—6 of FIG. 5;

FIG. 7 illustrates a sectional view of an alternative embodiment of a three-component anastomotic fitting;

DESCRIPTION OF PREFERRED EMBODIMENTS

Figure 1:
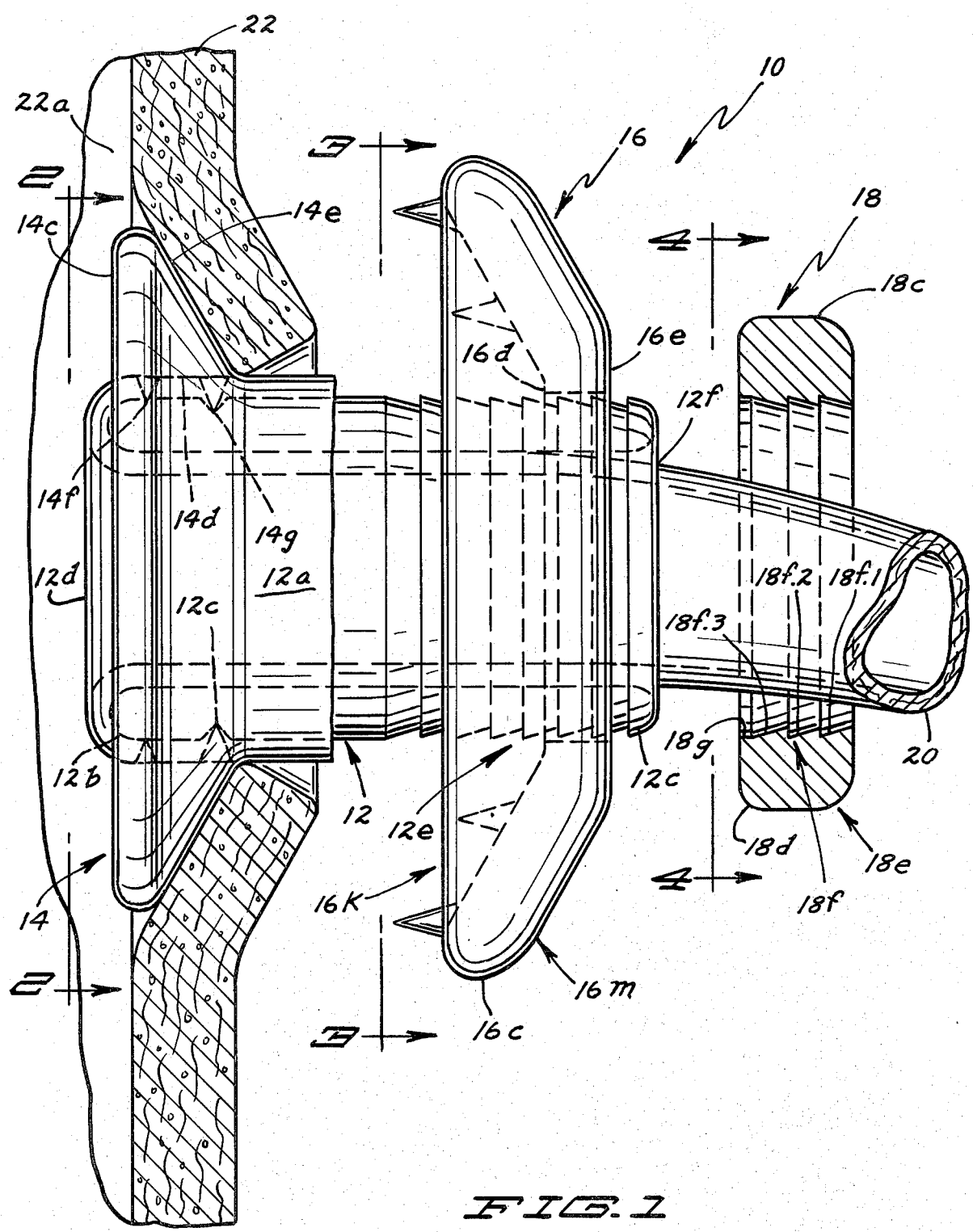
FIG. 1 illustrates an exploded view of an anastomotic fitting including a tube, a ringflange, a fixation ring, and a locking ring where the tube is engaged through a hole in the aortic wall and a saphenous vein is engaged therebetween.

FIG. 1, which illustrates an exploded view of the components of an anastomotic fitting 10 of the present invention, shows an anastomotic fitting 10 including tube 12, ringflange 14, a fixation ring 16 and a locking ring 18, about a saphenous vein 20 and engaged in a hole 22a in an aortic wall 22 having a hole 22a where all elements are now described in detail.

The tube which is a short hollow right cylinder 12a having an internal surface which is smooth and both ends 12b and 12c which are rounded having a radius of curvature equal to one-half of the wall thickness. Concentric grooves are disposed on an external surface as now described. One type, a ringflange indentation 12c is positioned substantially within 2 millimeters (mm) of the inflow end 12d of the tube. The bottom of the groove 12c is rounded and the sides of the groove are angled approximately 30 degrees to the plane normal to the central axis of the tube 12.

Locking ring grooves 12e including a plurality of identical grooves in the range of five to ten extend about half of the external surface of the tube from the mid-region to the outflow end 12f and have a geometrical saw-tooth configuration. One side of each groove is substantially normal, 85 degrees to 95 degrees, to the central axis of the tube 12. The other side of each of these grooves is inclined at an angle of 15 degrees to the central axis or in the range of 10°-20°.

A representative tube 12 substantially measures 8.0 mm in length, 5.0 mm across its outside diameter, 3.5 mm across its inside diameter and 0.75 mm of wall thickness. Because grafts with varying dimensions are used as coronary artery bypass grafts, several sizes of anastomotic fittings including the tube 12 are required. Therefore, the range of dimensions of the tube 12 substantially encompass the following: 5.0 mm to 10.0 mm in length, 4.0 mm to 7.0 mm across the outside diameter, 2.5 mm to 5.5 mm across the inside diameter, and 0.6 mm to 1.5 mm of wall thickness.

FIG. 2, which illustrates a sectional view taken along line 2—2 of FIG. 1, shows the ringflange 14 including a circular member 14a with a concentric central aperture 14b. The surfaces of the ringflange 14 are best disclosed by viewing the cross-sectional view seen of FIG. 1 in light of FIG. 2. The cross-sectional geometry is that of a right triangle with the side of the triangle being equal to or longer than the base. In respect to the three sides of a triangle, the side is known as the blood surface 14c, the base is referred to as the graft surface 14d and the hypotenuse as the aortic wall surface 14e. Except for the graft surface, the blood and aortic wall surfaces are flat and without significant irregularities or extensions. The angle between the side and hypotenuse measures 30 degrees and in the range of 20°-40°. This edge or angle between the blood and aortic wall surfaces is rounded with a radius of curvature in the range of 0.35 mm to 0.5 mm. Structurally, the graft surface 14d is a complex geometrical surface. Two rows of spikes 14f and 14g project towards the central axis of the ringflange from the graft surface in FIGS. 1 and 2 where the spikes are uniformly distributed in two rows around the central aperture. While there are substantially ten spikes in each row, by way of example and for purposes of illustration only, and not to be construed as limiting of the present invention, there can be a lesser or greater number of spikes in both rows. The number of spikes per row can range from 4 to 15 depending upon the diameter 14b of the central aperture and width of each of the spikes at the base 14d. Generally, the spikes or row 14g are substantially twice the size (base, height and width) as the spikes of the row 14f. Typically, the longer spikes 14g of a ringflange measure 0.58 mm while the shorter length spikes 14f measure about 0.33 mm. The spikes 14f and 14g can be described as having the shape of a right cone with the tip of the spike being the apex of the cone where each spike has a substantially apex or vertex angle of 50 degrees.

Representative external dimensions of the ringflange 14 by way of example include an external diameter of 10.00 mm, a central aperture diameter of 5.65 mm and a thickness that measures 1.75 mm. Several sizes of anastomotic fittings are required because grafts of varying dimensions are frequently encountered during coronary bypass surgery. Therefore, the measurements of the ringflange substantially range as follows: 7.0 mm to 15.0 mm outside diameter, 4.65 mm to 7.65 mm central aperture diameter and 1.25 mm to 2.75 mm thick.

The ringflange is not continuous around its entire circumference as a slit 14h of very small width of substantially 0.4 mm or less transects the cross-section. This single slit 14h allows the ringflange 14 to be flexed or expanded providing for engagement on the tube 12 exhibiting characteristics as a spring clamp and including forceps holes 14i and 14j. Alternatively, the cross-section of the ringflange 14 can be transected in two places resulting in a two-part component.

FIG. 3, which illustrates a sectional view taken along line 3—3 of FIG. 1 shows the fixation ring 16 is a circular member 16a having a concentric central aperture 16b. The geometrical shape of the fixation ring 16 is that of a shallow truncated right cone having a vertex angle of substantially 120 degrees. The outermost circumferential edge 16c as illustrated in FIG. 1 is rounded so that the inner surface blends smoothly with the outer surface. The surface 16d of the central aperture is flat and substantially perpendicular to the central axis of the fixation ring 16. The outer surface 16e of the fixation ring 16 is generally smooth and without significant irregularities or projections. Both inner and outer surfaces are parallel to each other, but parallelism is not essential or required. A narrow graft surface margin 16d of approximately 0.2 mm width concentrically encircles the central aperture. The plane of this surface margin is normal to the central axis of the fixation ring. A wide surface locking ring abutment margin 16e measures about 1 mm wide and concentrically encircles the central aperture. The plane of this wide surface margin 16e is parallel to the narrower margin 16d on the opposite side of the central aperture and is normal to the central axis of the fixation ring.

The measurements of a representative fixation ring are as follows: 12.0 mm outside diameter, 5.1 mm central aperture diameter, and 1.25 mm wall thickness. Because grafts of varying dimensions are used as coronary artery bypass grafts, several sizes of anastomotic fittings are required. Therefore, the measurements of the fixation ring 16 can range on both sides of the representative figures set forth above as follows: 8.0 mm to 16.0 mm outer diameter, 4.1 mm to 7.1 mm central aperture diameter, and 0.4 mm to 2.0 mm wall thickness. The central aperture diameter 16b is slightly larger than the outside diameter of the tube 12.

A plurality of individual spikes extend from a spiked aortic wall inner surface 16f of the fixation ring 16 where the spikes project parallel to the central axis of the fixation ring 16. While the spikes are of the same length and are arranged into two concentric circular rows in an innermost row 16g and an outermost row 16h, it is not essential that all of the spikes be of the same length or arranged in concentric circular rows as such is by way of example and for purposes of illustration only. The tips 16j of the spikes in the outermost row extend beyond the conical base plane of the fixation ring 16. The outermost circular row 16h of spikes is located about 1 mm from the outermost peripheral circumference of the fixation ring 16 and the innermost circular row 16g of spikes is located between 1 mm and 2 mm from the circumferential edge of the central aperture. In this embodiment, there are twice the number of spikes in the outermost row 16h than in the innermost row 16g, but this is not essential for operation. Each of the spikes is conical in shape having a vertex angle of about 20° and having a length 0.8 mm to 1.0 mm in length, but conical shape is not essential for operation.

FIG. 4, which illustrates a sectional view taken along line 4—4 of FIG. 1, shows the locking ring 18 including circular member 18a with a concentric aperture 18b. The locking ring 18 includes an outer circumferential surface 18c which in FIG. 1 is flat and parallel to the central axis of locking ring 18. Both edges 18d and 18e of the circumferential surface are rounded with radii of 0.25 mm and 0.75 mm respectively and the plane of each face of the locking ring 18 is normal to the central axis where the planes of the two faces are parallel. The central aperture 18b includes three concentric ridges 18f. Two of the three ridges 18f.1 and 18f.2 are the mirror image of the locking ring grooves 12e found on the external surface of the tube 12. On the leading edge of the third ridge 18f.3 is a narrow margin 18g whose diameter is slightly larger, of 0.1 mm or more, than the outside diameter of the tube 12. Consequently, the width of the locking ring 18 is the additive result of three locking ring grooves 18f and the width of the narrow leading edge margin 18g.

Dimensions of the central aperture 18b are most important to achieve a proper assembled result between the components of the anastomotic fitting 10, the aortic wall 22 and the graft 20. None of the external dimensions are critical to the end result except that the locking ring 18 retain structural integrity and firmness when in assembled relationship with the other component parts of the anastomotic fitting 10. Several sizes of this anastomotic fitting are necessary because grafts of varying dimensions are frequently encountered during coronary bypass surgery and therefore, the dimensions range in accordance with different size fittings.

Like the ringflange 14, the locking ring 18 is not continuous around its entire circumference. A slot 18h of very small width of about 0.4 mm or less transects the cross-section and includes forceps holes 18i and 18j positioned about either side. This single slit 18h allows the locking ring 18 to be flexed or expanded providing easy assembly on the tube 12. In this way the locking ring 18 behaves as a spring clamp.

Each component 12-18 of the four component anastomotic fitting 10 as well as the assembled anastomotic fitting 10 must exhibit predetermined physical, mechanical and dimensional characteristics. A number of the characteristics can be inherent in the construction material. These features include radio-translucence, blood compatability, tissue compatibility, light weight and small size. The tube 12 and fixation ring 14 are passive components. The ringflange 16 and locking ring 18 are active components that need to be flexed or expanded during implant. Therefore, these latter components are constructed of material that exhibits a spring-like quality and a permanent dimensional memory.

Some of the suitable construction materials for these components are Pyrolite, ceramic, sapphire, metals including titanium, tantalum, or stainless steel, etc., or plastics including Teflon, polycarbonate, polysulfone, polypropylene, etc. Pyrolite, titanium, tantalum, stainless steel, Teflon, polycarbonate and polypropylene have all been previously utilized in medical products. Pyrolite and titanium have recorded very suitable long-term histories as cardiovascular implant materials. Pyrolite exhibits an excellent spring-like quality, is fatigue resistant and has a permanent memory. The final selected construction material(s) of the components of this device will have been evaluated for these and other characteristics.

MODE OF OPERATION

Anastomotic fitting or fittings which are to be implanted are predetermined by the location of the coronary artery blockage, surgical accessibility of the downstream coronary arteries, and size of the downstream coronary arteries where a graft or grafts are implanted for best surgical result. While in most cases a surgeon will implant two or three bypass grafts in each patient who undergoes coronary artery bypss surgery, for purposes of illustration and for example only the description of the mode of operation is limited and directed to an implant of one bypass graft, and is not to be construed as limiting of the present invention as the description can be extended to more than one bypass graft implant as required as illustrated in FIG. 5 or implant of a graft of a first diameter to a blood vessel of a second diameter as illustrated in FIG. 6, a sectional along line 6—6 of FIG. 5.

FIG. 5 illustrates a plan view of two anastomotic fittings 10 and 24 positioned in the aortic wall, and at an angular relationship with respect to each other.

The anastomotic fitting 10 of the present invention can be used to connect both biologic as well as synthetic vascular grafts to blood vessels of generally larger diameter. In this example, a saphenous vein graft 20 is connected between the ascending aorta 22 and, remotely, to a coronary artery to bypass blood around a blocked coronary artery. The connections of the saphenous vein graft to the aorta and coronary artery are known as the proximal anastomosis and distal anastomosis respectively. This embodiment pertains to the proximal anastomosis for which the anastomic fitting 10 is best suited. The following steps are necessary for assembling and installing the anastomotic fitting 10.

The inside diameter of the vein graft near the end that is attached to the aortic wall is gauged with a sizing-obturator. The anasomotic fitting 10 is chosen whose tube 12 has an inside diameter that approximates the outside diameter of the vein graft. The gauged end of the vein graft is passed through the tube 10 from the outflow end 12f to the inflow end 12d or, into the end with the numberous locking ring grooves and out of the end with the single ringflange indentation. The leading end of the graft projecting through the inflow end of the tube is everted over the outside of the tube 10 for an approximate distance of three millimeters. Care is taken not to extend the graft over the locking ring grooves 12e. If necessary, the graft is trimmed about one millimeter short of the first locking ring groove. The tubed-/graft is ready to receive the ringflange 14. Remembering that a slit through the cross-section allows it to be expanded, the ringflange 14 is expanded using a surgical instrument such as a forceps. The blood surface of the ringflange 14 is placed down on a firm flat surface. The tapered ends of the forceps are inserted, each, into a hole located on either side of the slit 14, of the aortic wall surface. The ring 14 is caused to expand by spreading or opening the forceps the same as one opens a pair of pliers. The inflow end of the tubed-graft with the everted graft is placed into the expanded central aperture 14b of the ringflange 14. Care is taken to be certain that the end of the tubed-graft is in complete circular contact with, and perpendicular to, the firm flat surface beneath the ringflange 14. The ringflange 14 and tubed-graft are then in correct spatial relation for engagement of the latter by the spikes 14f and 14g of the ringflange 14. The opening force on the forceps and consequently on the ringflange is relaxed. The spring-clamp characteristic of the ringflange 14 causes it to close and clasp the tube 12, in a firm positive manner. All of the spikes 14f and 14g projecting from the graft surface of the ringflange penetrate the thickness of the graft 20 and engage the surface of the tube 12. The tips of the smaller spikes 14f puncture the graft and immediately engage the external surface of the tube 12. A substantial portion of the tip end of the larger spikes 14g penetrates the graft thickness. The tips come to rest in the bottom of the ringflange indentation 12c. Proper placement of the ringflange 14 occurs when the slit has returned to or near its pre-engagement relaxed width and the spikes 14f and 14g in both encircling rows engage the surface of the tube 12. The clasping characteristic of the ringflange 14 is expected to produce a satisfactory capture of the graft 20 and tube 12 from engagement by the spikes. This assembly is now attached to the aortic wall. A hole having a diameter equal to or slightly larger but not more than one millimeter larger than the outside diameter of the tube is made in the predetermined place in the aortic wall. The hole is made using a hole-punch especially designed for this purpose.

Because blood is an excellent lubricant, and is readily accessible in the operative field, the ringflange 14 is wetted with blood to facilitate and ease its passage through the smaller diameter aortic wall hole. Grasping the tube near its outlow end, the peripheral edge of the ringflange is positioned at the center of the hole and angled substantially 30 degrees relative to the plane of the hole. The leading peripheral edge of the ringflange is then advanced into the hole and with a firm continuous twisting motion and is engaged into the aortic lumen. As a result, the free edge of the graft 20 may have to be adjusted and continuing, therefore, to grasp the outflow end 12f of the tube 12, the assembly is gently retracted until the ringflange 14 engages the inside of the aortic wall 22 causing the peripheral edge of the hole to bulge outward in response to the angulation of the aortic wall surface of the ringflange 14 as illustrated in FIG. 1. With a pair of forceps or similar surgical instrument, the free-edge of the graft 20 is restored to its preinsertion symmetry on the outside of the surface of the tube 12. The proper lay of the graft and the relationship to the edge of the aortic wall hole is illustrated in FIG. 6. The Figure also illustrates the correct angulation of the periphery of the aortic wall hole 22a.

Next, the outflow end of the graft is passed through the central aperture 16b of the fixation ring 16 from the base side 16k to the apex side 16m. Holding the entire length of the graft under gentle tension, the fixation ring 16 is then easily advanced from the distal end of the graft to the outflow end 12f of the tube 12 without entangling the graft in the long spikes 16h and 16g of the fixation ring 16. The inside diameter of the central aperture of the fixation ring 16 is slightly larger than the outside diameter of the tube 12. This provides free movement of the fixation ring along the length of the tube.

The fixation ring is advanced from the outflow end of the tube to the aortic wall 22, but, it is not yet advanced against the aortic wall 22. Grasping the outflow end of the tube, the assembly is gently retracted normal to the plane of the hole resulting in centering and aligning the assembly of the ringflange and tube with the hole 22a in the aortic wall 22 and causing the aortic wall to be uniformly distributed over the surface of the hypotenuse 14e of the ringflange 14. Continuing, the fixation ring is advanced against the aortic wall and care is exercised in firmly pressing the fixation ring into complete contact with the aortic wall surface. Hence, all of the spikes 16g and 16h have penetrated their full allowable distance into the thickness of the aortic wall.

The average thickness of the aortic wall 22 is about 1.2 millimeters. In the surgically complete anastomotic fitting, it is desirable that the tips of the spikes 16g and 16h of the fixation ring 16 remain within the tissue of the aortic wall. Therefore, the spikes are limited to a length of one millimeter or less. The conical shape of the spike effectively impacts the spike in the aortic wall tissue and eliminates the possibility of blood escaping along its surface. The area of impacted tissue around and along the length of the spike is small near the tip and becomes more broad near the base of the spike. However, none of the impacted tissue is isolated from the vascular bed in the aortic wall. Therefore, this tissue will remain viable.

A narrow circular margin, measuring two millimeters to three millimeters, of aortic tissue around the hole 22a is placed under constant but slight compression between opposing surfaces of the ringflange 14 and the fixation ring 16. In effect, the free spaces between the aortic wall, the graft and the three components of the anastomotic fitting are markedly reduced, and can even be eliminated where the elimination of these spaces in combination with the slight compressive force placed on the thickness of the aortic wall virtually eliminates the possibility of blood leakage along the interface between the aortic wall and the ringflange 14 and on outward along the interface between the edge of the hole in the aortic wall and the surface of the graft.

The locking ring 18 is the last component of the anastomotic fitting 10 to be installed. Observing the correct orientation of the locking ring 18 relative to the tube 12, the outflow end or free end of the graft 20 is passed through the central aperture of the locking ring 18. Grasping the free end of the graft and extending its length, the locking ring 18 is advanced the length of the graft to the outflow end of the tube 12. The leading edge 18g of the central aperture diameter is slightly larger than the outside diameter of the tube 12. That provides for initial movement and placement of the locking ring 18 onto the tube 12. The slit 18h through the cross-section of the locking ring 18 is expanded by using the surgical instrument forceps. The tapered ends of the forceps are inserted, each, into the holes 18i and 18j located on either side of the slit 18h of the distal surface. The ring 18 expands by spreading or opening the forceps the same as one opens a pair of pliers. Holding the ring 18 open, the ring is advanced along the length of the tube until it engages in firm abutting contact with the fixation ring 16. Care is exercised not to further compress the tissue of the aortic wall than that which was first accomplished during the placement of the fixation ring; however, it is essential that the initial compressive status not be relaxed. The ridges 18f–18f.3 engage in the grooves 12e as illustrated in FIG. 6.

On an event that disassembly of the anastomotic fitting is required, the spring feature of the locking ring 18 provides component removable by the same technique used for positioning. The clearance between the central aperture diameter of the fixation ring and the outside diameter of the tube permits the easy retraction of the fixation ring from the aortic wall and removal from the tube. The partial assembly of the tubed-graft and ringflange can be removed from the hole in the aortic wall by instituting the insertion motion in reverse. Finally, the ringflange can be removed from the end of the tube by, again, using the forceps to expand the ringflange. This provides removal of the tubed-graft from the ringflange.

Alternative Embodiment—Three—Component Anastomotic Fitting

FIG. 7, which illustrates a sectional view of an alternative embodiment of a three-component anastomotic fitting, shows a three-component anastomotic fitting 30. The components of the three-component anastomotic fitting 30 include a tube 32, a ringflange 34, and a latching-fixation ring 36. The tube 32 is of the same geometrical configuration as the tube 12 of the four-component anastomotic fitting but with two exceptions, where first, the tube 32 is about 10% shorter than tube 12 and second, the tube 32 can have one to three fewer latching grooves that encircle its downstream end 32f. The ringflange 34 of the three-component anastomotic fitting is identical to the ringflange 14 of the four-component device described earlier in FIGS. 1–6. The latching-fixation ring 36 is the third component of the anastomotic fitting 30 where the fixation ring 16 and locking ring 18 of the four-component anastomotic fitting 10 are combined to form the latching-fixation ring 36 of the three-component anastomotic fitting 30. Outwardly, the latching-fixation ring 36 exhibits the appearance of the fixation ring 16 described earlier but for two exceptions; one, the thickness of the central aperture from one side to the other is about ⅓ greater, and two, the surface of the central aperture has three concentric ridges that are dimensionally similar to those found in the central aperture of the locking ring 18 previously described in FIGS. 1–6.

Figure 8:
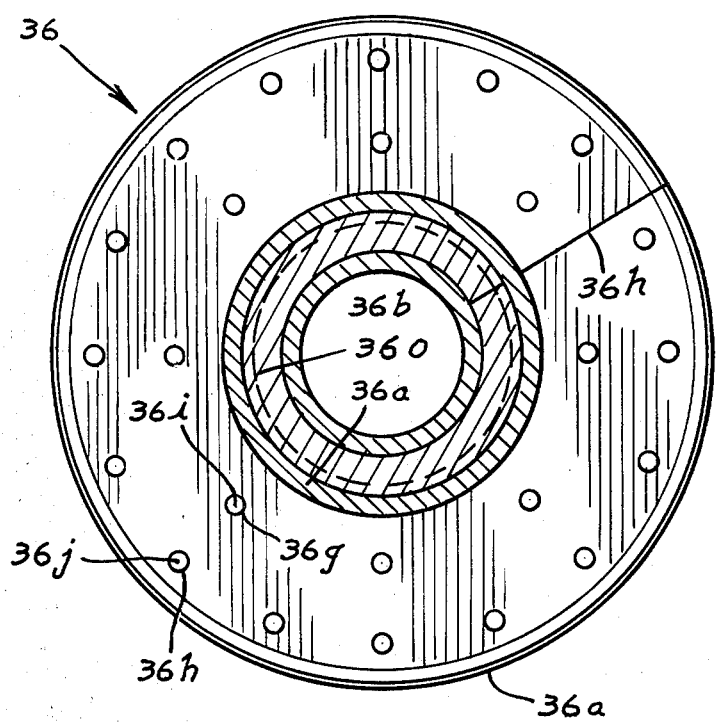
FIG. 8 illustrates a sectional view taken along line 8—8 of FIG. 7.

FIG. 8, which illustrates a sectional view taken along line 8—8 of FIG. 7, shows the latching fixation ring where all numerals correspond to those elements previously described. The latching-fixation ring 36 includes the locking ring ridge 36o, the narrow graft surface margin 36d, the aperture 36b, the rounded edge 36a, and the plurality of spikes 36g and 36h including tips 36i and 36j. The latching-fixation ring 36 also includes a slit 36h providing for engagement onto the tube 32.

Operation of the three-component anastomotic fitting 30 is similar to that as previously described for FIGS. 1–6 between the wall 42 and the graft 40.

The latching-fixation ring in FIG. 8 shows slit 36h across the cross-section like that of the previously discussed locking ring 18. The slit 36h enables expansion of the central aperture of the ring during engagement on the tube 32. The latching fixation ring can include at least one or more concentric grooves on the surface of the central aperture for latching as previously described. However, the slit 36h through the cross-section of the ring 36 may not be required depending upon the type of material and the desired physical and mechanical characteristics which the material exhibits.

Alternative Embodiment—Four-Component Anastomotic Fitting

Figure 9:
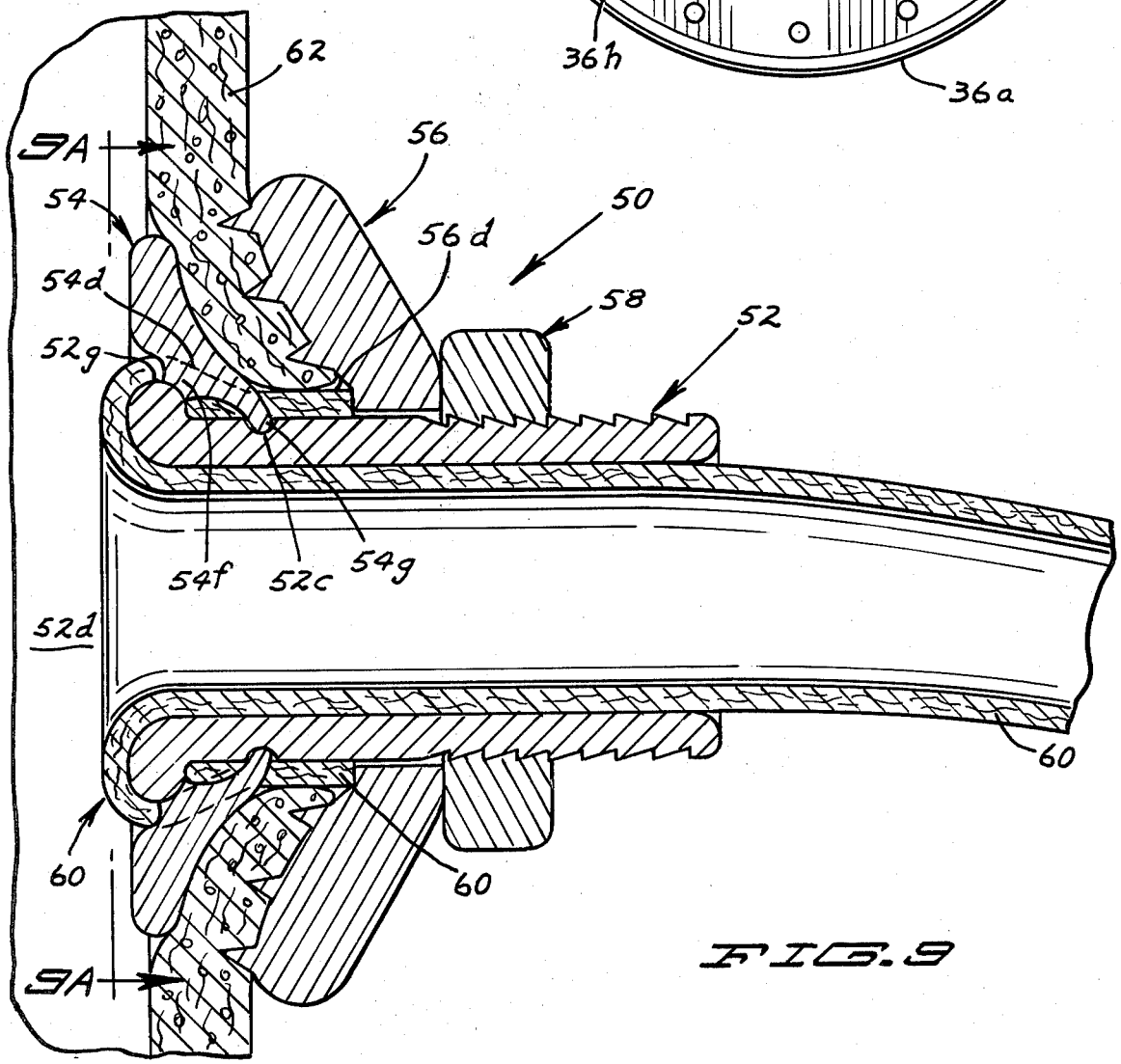
FIG. 9 illustrates a sectional view of an alternative embodiment of an anastomotic fitting; and, FIG. 9A illustrates a sectional view taken along line 9A—9A of FIG. 9.

FIG. 9, which illustrates a sectional view of an alternative embodiment of a four-component anastomotic fitting, shows the four-component anastomotic fitting 50. The components of the four-component anastomotic fitting 50 include a tube 52, a ringflange 54, a fixation ring 56, and a locking ring 58. The four-component anastomotic fitting has substantially the same essential components as that of the anastomotic fitting of FIGS. 1–6. However, the components 52–54 include certain geometrical variations as now described. The tube 52 and ringflange 54 exhibit the most notable geometrical variations. The inflow end 52d of the tube 52 is slightly flared having a lip 52g, yielding a larger exposure of graft material 60 at the anastomotic ostium. The structural geometrical variation of the tube 52 is reflected in the ringflange 54 which is modified for compatible engagement with the tube 52 and discussed in FIG. 9A. Consequently, the fixation ring 56 reflects slight but not essential geometrical modification from the previous fixation rings and the locking ring 58 is essentially unchanged. For purposes of brevity, and since similar structural elements such as grooves, spikes, surfaces, etc., have been previously described, previous description is referenced herein.

The ringflange 54 includes a circular member 54a having a concentric central aperture 54b. A graft surface 54d includes a plurality of spaced, short, generally rounded spikes 54f having a rounded indentation for engaging with the flared lip and long, rounded spikes 54g for engaging in the ringflange indentation 52c. The vascular graft engages over the flared lip 52g about the graft surface 54d, between the short spikes 54f and the flared lip 52g, between the long spikes 54g and the locking indentation 52c, and slightly beyond the outer circumference of the ringflange 54 and adjacent to a margin 56d of the fixation ring 56. The fixation ring 56 and the locking ring 58 are similar to those elements previously described, and explanation is referenced and incorporated herein.

Figure 9A:
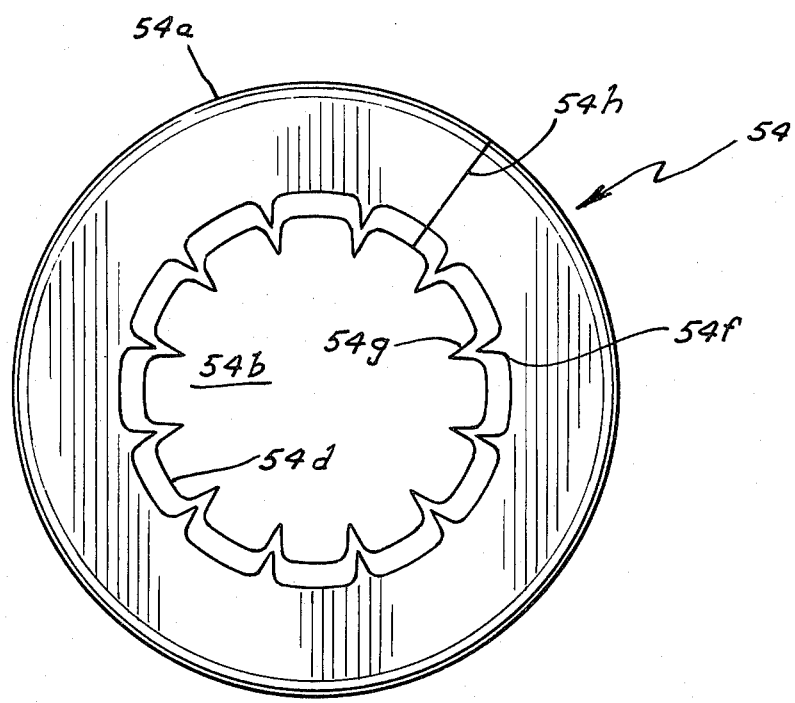

FIG. 9A illustrates a sectional view of the ringflange 54 where all numerals correspond to those elememts previously described. The ringflange 54 includes a slit 54h as previously discussed.

Operation of the anastomotic fitting 50 is similar to that as previously described for FIGS. 1–6 which explanation is referenced and incorporated herein between the wall 62 and the graft 60.

Various modifications can be made to the anastomotic fitting of the present invention without departing from the apparent scope thereof. The fixation ring can have material removed from the outer surface. The ringflange, locking ring, and combined fixation-locking ring can include holes on each side of the transecting slit for accepting a tied suture, similar mechanical latch, or contoured opposing interface surface providing for locking of the opposing faces and can be any other geometrical shape than circular such as hexagonal or octagonal.

Having thus described the invention, what is claimed is:

1. Anastomotic fitting for connecting a vascular graft to a blood vessel comprising:
   a. means for positioning in a hole between an inner and outer wall of a blood vessel including an inflow orifice, a section of cylindrical tube, and an outflow orifice serially, said means including a lumen for supporting a vascular graft through said positioning means and everting back about said inflow orifice, and at least one indentation groove and a plurality of external surface sawtooth locking rings outwardly extending grooves disposed on each of said inflow and outflow ends of said positioning means respectively;
   b. means including a cylindrical ring of triangular cross section for engaging said overlapped vascular graft and locked into said indentation adjacent said inflow end and engaged against an inside wall about said hole of said blood vessel, said engaging means including means for flexing cross-sectional area of said engaging means, and a plurality of spaced circumferentially long and short spike means projecting inwardly for engaging into said graft;
   c. means for affixing said positioning means including said affixing means having a plurality of spike means projecting inwardly from said affixing means for engaging an outside wall about said hole of said blood vessel; and,
   d. means for locking said affixation means to said positioning means, said locking means including means for engaging sawtooth locking ring inwardly extending grooves with said outwardly extending grooves of said positioning means and means for flexing cross-sectional area of said locking means at said outflow orifice of said positioning means whereby said anastomotic fitting provides a surgical connection between said vascular graft to said blood vessel and said short spike means engages said graft and said long spike means engaging into said indentation groove through said graft thereby securing said graft.

2. Anastomotic fitting of claim 1 wherein said positioning means comprises: tube including a short hollow right cylinder, a smoth internal surface, an inflow orifice at one end, a ringflange indentation disposed in an outer surface adjacent said inflow orifice, and at least one locking ring groove disposed in an outer surface adjacent an outflow orifice.

3. Anastomotic fitting of claim 2 wherein said number of locking ring grooves comprises five to ten.

4. Anastomotic fitting of claim 1 wherein said engaging means comprises: ringflange including a concentric central aperture, pluralities of short and long spikes extending inwardly from an interior diameter, said short spikes engage said overlapped vascular graft and said long spikes engage through said vascular graft into said indentation at said outflow end.

5. Anastomotic fitting of claim 4 wherein said flexing means comprises a slit through cross-section of said member whereby said slit facilitates engagement about said tube.

6. Anastomotic fitting of claim 1 wherein said affixing means comprises: member including a central aperture and pluralities of spikes extending outwardly from an angular face of said member whereby said central aperture engages with said positioning means and said pluralities of spikes engage against said blood vessel wall.

7. Anastomotic fitting of claim 1 wherein said locking means comprises: member including a central aperture and at least one locking ridge extending inwardly from an interior diameter of said member whereby said locking ring ridge engages against said groove disposed on said outflow end of said positioning means.

8. Anastomotic fitting of claim 7 wherein said number of locking ring ridges comprise one to three.

9. Anastomotic fitting of claim 7 wherein said flexing means comprises a slit through said cross-section of said member whereby said slit facilitates engagement about said positioning means.

10. Anastomotic fitting of claim 1 wherein said affixation means and said locking means comprises:
    a. integral member including member including a concentric central aperture, pluralities of spikes extending outwardly from an angular face of said member; and,
    b. at least one locking ridge extending inwardly from an interior diameter of said circular member whereby said central aperture engages with said positioning means, said pluralities of spikes engage against said blood vessel and said locking ring ridge engages against said groove disposed on said outflow end of positioning means.

11. Anastomotic fitting of claim 10 wherein said flexing means comprises a slit through cross-section of said integral member whereby said slit facilitates engagement about said positioning means.

12. Anastomotic fitting of claim 1 wherein said positioning means and said engaging means comprise:
    a. said positioning means further comprises a flared lip at said inflow orifice;
    b. said engaging means comprises a member including circular geometrical configured interior diameter including inversely rounded short spikes for engagement over said flared end and rounded long spikes for engagement in said indentation adjacent said inflow end.

13. Anastomotic fitting of claim 12 wherein said flexing means comprises a slit through cross-section of said circular geometrically configured engaging means member whereby said slit facilitates engagement about said positioning means.

14. Anastomotic fitting for coronary artery bypass surgery for connecting a vascular graft or reconnecting a vessel of a first diameter to a vessel of a second diameter, said anastomotic fitting comprising:
    a. cylindrical tube including a lumen extending therethrough, serially, a ringflange circumferential indentation adjacent an inflow end of said tube, a longitudinal section of said tube, and plurality of external surface sawtooth locking ring grooves spaced and adjacent an external surface of an outflow end of said tube from said inflow end to said outflow end;
    b. ringflange including a cross-sectional slitted member and a concentric central aperture therethrough, plurality of inwardly extending short spikes on a first circumference and long spikes on a second circumference spaced from said first circumference, said short spikes engaging said vascular graft at a plurality of points and said long spikes engaging through said vascular graft into said ringflange indentation, said ringflange engaged against an inside vessel and over an end of said vascular graft;
c. fixation ring including a truncated conical member and a concentric central aperture therethrough, pluralities of inwardly extending spikes about an internal surface of said truncated conical member partially engaged into an outside vessel wall; and,
d. locking ring including a cylindrical ring member and a concentric central aperture therethrough, a plurality of inwardly extending sawtooth locking ring ridges for engaging with said outwardly extending grooves of said cylindrical tube, and a cross-sectional slit therethrough whereby said anastomotic fitting provides a surgical connection between said vascular graft to said blood vessel.

15. Anastomotic fitting for coronary artery bypass surgery for connecting a vascular graft or reconnecting a vessel of a first diameter to a vessel of a second diameter, said anastomotic fitting comprising:
a. cylindrical tube of longitudinal length including a lumen extending therethrough, serially, a ringflange circumferential indentation adjacent an inflow end of said tube and plurality of external surface sawtooth locking ring grooves spaced and adjacent an outflow end of said tube;
b. ringflange including a cross-sectional slitted member and a concentric central aperture therethrough, plurality of inwardly extending short spikes on a first circumference and long spikes on a second circumference spaced from said first circumference, said short spikes engaging said vascular graft at a plurality of points and said long spikes engaging through said vascular graft into said ringflange indentation, and said ringflange engaged against an inside vessel wall and over an end of said vascular graft; and,
c. fixation ring-locking ring including a truncated right conical member and a concentric central aperture therethrough, pluralities of outwardly extending spikes partially engaged into an outside vessel wall, a plurality of inwardly extending locking ring sawtooth ridges, and a cross-sectional slit therethrough whereby said inwardly extending grooves engage with said external grooves for locking said fixation ring-locking ring to said cylindrical tube with said vessel therebetween, thereby providing a surgical connection between said vessel and said vascular graft.

* * * * *